United States Patent [19]
Saito et al.

[11] Patent Number: 6,072,082
[45] Date of Patent: Jun. 6, 2000

[54] PROCESS FOR PRODUCING 2,2'-BIS (HYDROXYMETHYL) ALKANOIC ACID

[75] Inventors: Hideshi Saito; Mikio Suzuki; Shoji Sakamoto, all of Iwaki; Toshiharu Yokoyama; Kouji Maeda, both of Yokohama, all of Japan

[73] Assignee: Nippon Kasei Chemical Company, Fukushima-ken, Japan

[21] Appl. No.: 09/246,964

[22] Filed: Feb. 9, 1999

[30] Foreign Application Priority Data

Feb. 18, 1998 [JP] Japan ................................ 10-52978

[51] Int. Cl.[7] ............................ C07C 51/16; C07C 59/10
[52] U.S. Cl. ............................................. 562/531; 562/587
[58] Field of Search ................................... 562/531, 587

[56] References Cited

U.S. PATENT DOCUMENTS

| | | |
|---|---|---|
| 3,312,736 | 4/1967 | Ruhf . |
| 4,233,247 | 11/1980 | Immel et al. . |
| 4,247,485 | 1/1981 | Immel et al. . |

FOREIGN PATENT DOCUMENTS

| | | |
|---|---|---|
| 0 004 577 | 10/1979 | European Pat. Off. . |
| 0 860 419 A1 | 8/1998 | European Pat. Off. . |
| 2 301 505 | 9/1976 | France . |
| 2 395 670 | 10/1978 | France . |

OTHER PUBLICATIONS

Abstract: Derwent No. XP002066204 and JP 09295956, "Preparation of 2,2'–bis (hydroxy:methyl) alkanal . . . . " (1997).

*Primary Examiner*—Joseph McKane
*Assistant Examiner*—Joesph Murray
*Attorney, Agent, or Firm*—Nixon & Vanderhye

[57] ABSTRACT

A process for producing 2,2'-bis(hydroxymethyl)alkanoic acid of the present invention, comprises:

a 2,2'-bis(hydroxymethyl)alkanal production step (A1) of reacting aliphatic aldehyde having two hydrogen atoms bonded to α-carbon atom thereof, with formaldehyde in the presence of a water-soluble base;

a 2,2'-bis(hydroxymethyl)alkanoic acid production step (B) of subjecting the thus obtained aqueous solution (a) containing 2,2'-bis(hydroxymethyl)alkanal and the base to oxidation treatment; and an alkanoic acid recovery step (C) of separating 2,2'-bis (hydroxymethyl)alkanoic acid from the thus obtained aqueous solution (b) containing the 2,2'-bis (hydroxymethyl)alkanoic acid and the base, in the alkanoic acid recovery step (C), a mineral acid being added to the aqueous solution (b) in an amount of not more than one equivalent based on the base in the aqueous solution (b) to convert the base into a salt thereof, water in the aqueous solution (b) being replaced with an organic solvent to form an organic solvent solution, and after removing the mineral acid salt precipitated from the organic solvent solution, 2,2'-bis(hydroxymethyl) alkanoic acid being crystallized from the organic solvent solution.

8 Claims, 1 Drawing Sheet

FIG.1

PROCESS FOR PRODUCING 2,2'-BIS (HYDROXYMETHYL) ALKANOIC ACID

BACKGROUND OF THE INVENTION

The present invention relates to a process for producing 2,2'-bis(hydroxymethyl)alkanoic acid, and more particularly to, an industrially useful process for producing 2,2'-bis (hydroxymethyl)alkanoic acid, which process includes an improved step for recovery of the alkanoic acid. The 2,2'-bis(hydroxymethyl)alkanoic acid (hereinafter referred to merely as "dimethylol alkanoic acid") can be produced by the oxidation of 2,2'-bis(hydroxymethyl)alkanal (hereinafter referred to merely as "dimethylol alkanal"), and is useful as a raw material for the production of polyesters, polyurethanes, alkyd resins or the like.

The dimethylol alkanal can be obtained by condensation-reacting aliphatic aldehyde having two hydrogen atoms bonded to α-carbon atom thereof, with an appropriate amount of formaldehyde in the presence of a base (refer to the following reaction formula (I)). Upon the condensation reaction, 2-substituted acrolein is by-produced. Alternatively, the dimethylol alkanoic acid can be produced by the oxidation of dimethylol alkanal (refer to the following reaction formula (II)). The by-produced 2-substituted acrolein is converted into dimethylol alkanal by reacting with an appropriate amount of formaldehyde in the presence of a base (refer to the following reaction formula (III)).

As the bases (condensation catalysts) used in the production of dimethylol alkanal, there have been proposed sodium hydroxide (Japanese Patent Publication (KOKOKU) No. 52-20965(1977) and Japanese Patent Application Laid-open (KOKAI) No. 62-263141(1987)), sodium carbonate (U.S. Pat. No. 3,312,736), triethylamine (Japanese Patent Publication (KOKOKU) No. 4-55181(1992)), dimethylamino neopentanol (German Patent No. 2,507,461) or the like.

Specifically, for example, in U.S. Pat. No. 3,312,736, there is described a process in successive steps from the production of dimethylol alkanal to the recovery of dimethylol alkanoic acid, comprising reacting n-butyl aldehyde with formaldehyde in a water solvent in the presence of sodium carbonate, treating the reaction solution with hydrogen peroxide, removing inorganic substances derived from sodium carbonate, from the reaction solution using sulfonate-type cation exchange resin, subjecting the reaction solution to evaporation treatment, and cooling and then filtering the reaction solution to obtain 2,2'-bis (hydroxymethyl)butanoic acid as a solid.

However, in the above-mentioned conventional process, a large amount of wash water is required to regenerate the cation exchange resin, so that a large amount of waste water must be treated subsequently, which is extremely disadvantageous from the industrial viewpoint.

As a result of the present inventors' studies, it has been found that in an alkanoic acid recovery step, by adding a mineral acid to an aqueous solution containing the 2,2'-bis (hydroxymethyl)alkanoic acid and the base, in an amount of not more than one equivalent based on the base in the aqueous solution to convert the base into a salt thereof; adding an organic solvent to the aqueous solution to replace water in the aqueous solution with an organic solvent, thereby forming an organic solvent solution; and after removing the mineral acid salt precipitated from the obtained organic solvent solution, crystallizing 2,2'-bis (hydroxymethyl)alkanoic acid from the organic solvent solution, 2,2'-bis(hydroxymethyl)alkanoic acid can be recovered in a high yield. The present invention has been attained in the basis of the finding.

SUMMARY OF THE INVENTION

It is an object of the present invention to provide an industrially useful process for producing 2,2'-bis (hydroxymethyl)alkanoic acid, which process includes an improved step for the recovery of 2,2'-bis(hydroxymethyl) alkanoic acid.

It is another object of the present invention to provide a process for producing 2,2'-bis(hydroxymethyl)alkanoic acid, which process is capable of reducing a load for recovering unreacted formaldehyde and decreasing an amount of residual formaldehyde, thereby producing 2,2'-bis(hydroxymethyl)alkanoic acid with a high yield.

To accomplish the aim, in a first aspect of the present invention, there is provided a process for producing 2,2'-bis (hydroxymethyl)alkanoic acid, comprising:

a 2,2'-bis(hydroxymethyl)alkanal production step (A1) of reacting aliphatic aldehyde having two hydrogen atoms bonded to α-carbon atom thereof, with formaldehyde in the presence of a water-soluble base;

a 2,2'-bis(hydroxymethyl)alkanoic acid production step (B) of subjecting the thus obtained aqueous solution (a) containing 2,2'-bis(hydroxymethyl)alkanal and the base to oxidation treatment; and an alkanoic acid recovery step (C) of separating 2,2'-bis (hydroxymethyl)alkanoic acid from the thus obtained aqueous solution (b) containing the 2,2'-bis (hydroxymethyl)alkanoic acid and the base, in the alkanoic acid recovery step (C), a mineral acid being added to the aqueous solution (b) in an amount of not more than one equivalent based on the base in the aqueous solution (b) to convert the base into a salt thereof, water in the aqueous solution (b) being replaced with an organic solvent to form an organic solvent solution, and after removing the mineral acid salt precipitated from the organic solvent solution, 2,2'-bis(hydroxymethyl)alkanoic acid being crystallized from the organic solvent solution.

DETAILED DESCRIPTION OF THE INVENTION

The present invention is described in detail below. The process for producing dimethylol alkanoic acid comprises at least an alkanal production step (A1), an alkanoic acid production step (B) and an alkanoic acid recovery step (C). In the present invention, the alkanoic acid recovery step (C) comprising a crystallization method including a specific pre-treatment.

In accordance with the first preferred embodiment of the present invention, the process further comprises an alkanoic acid re-recovery step (D) of adding an aqueous solution of inorganic base to an organic solvent solution recovered by liquid-solid separation after the crystallization and containing uncrystallized alkanoic acid, thereby converting the alkanoic acid into a salt thereof, and then eluting (distilling off) water from a water phase separated from the organic solvent solution, thereby recovering the alkanoic acid salt.

In accordance with the second preferred embodiment of the present invention, the process further comprises an alkanal production step (A2) of reacting formaldehyde with 2-substituted acrolein by-produced in the alkanal production step (A1), in a water solvent in the presence of a water-soluble base.

In addition, in accordance with the third preferred embodiment of the present invention, the process further comprises an acrolein separation step (E) of recovering a 2-substituted acrolein-rich component from the reaction solution of the alkanal production step (A1), and a 2,2'-bis (hydroxymethyl)alkanal production step (A2) of reacting formaldehyde with the 2-substituted acrolein recovered in the acrolein separation step (E), in a water solvent in the presence of a water-soluble base. At least a part of the formaldehyde-containing reaction solution produced in the 2,2'-bis(hydroxymethyl)alkanal production step (A2), is circulated to the alkanal production step (A1). The respective steps of the third preferred embodiment may be conducted in a continuous manner.

Figure 1:
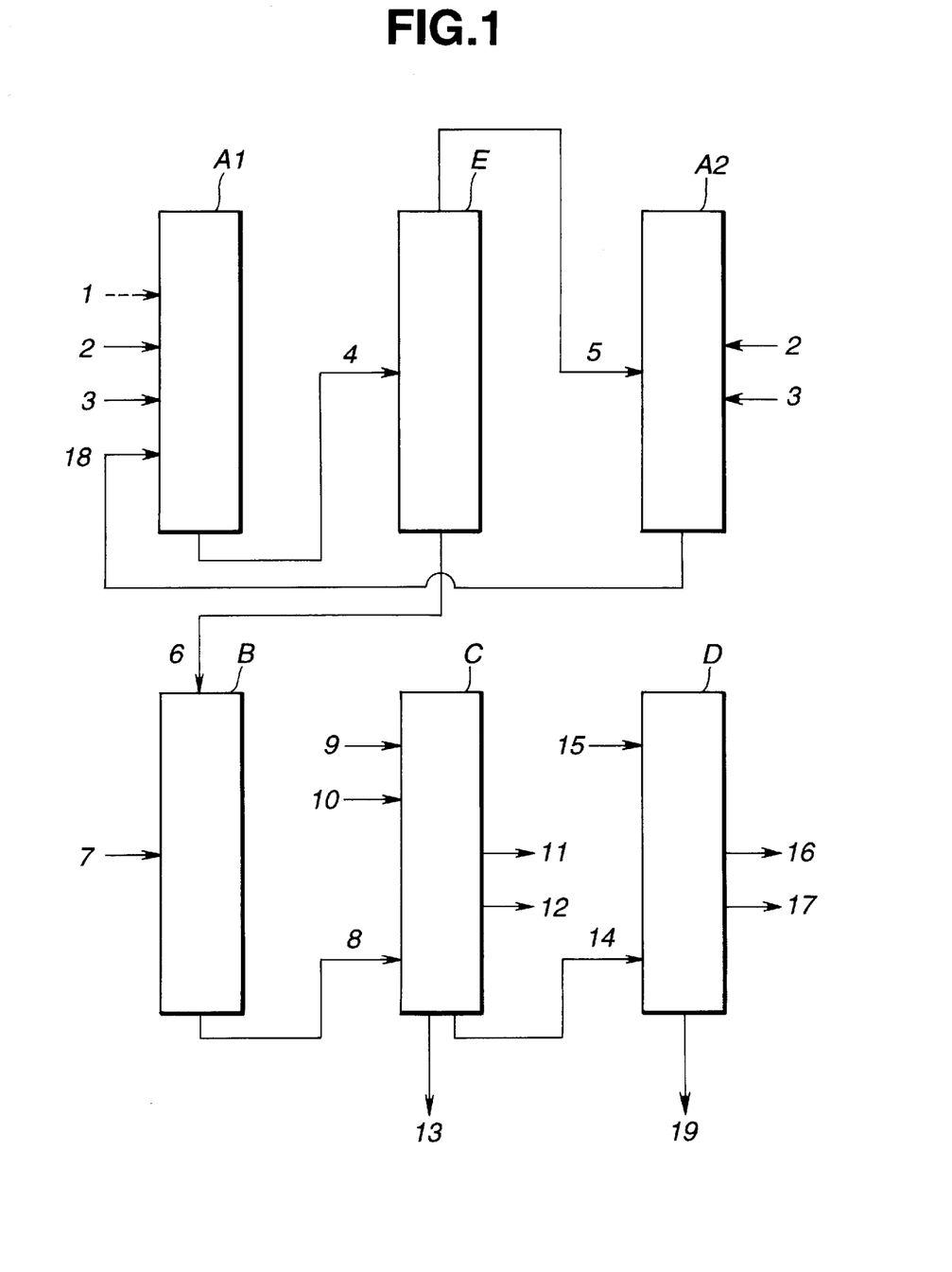
FIG. 1 is a flow diagram showing an example of a continuous production process according to the preferred embodiment of the present invention.

First, the alkanal production step (A1) is explained below. In the step (A1), an aliphatic aldehyde having two hydrogen atoms bonded to α-carbon atom thereof (hereinafter referred to merely as "aliphatic aldehyde"), is reacted with formaldehyde in a water solvent in the presence of a water-soluble base, thereby producing alkanal. Simultaneously, 2-substituted acrolein is by-produced in the step (A1). In FIG. 1, aliphatic aldehyde (1), formaldehyde (2) and a water-soluble base (condensation catalyst) (3) are supplied to the alkanal production step (A1).

The aliphatic aldehyde used in the present invention is represented by the general formula: R—$CH_2CHO$, wherein R is a substituted or unsubstituted straight-chain or branched saturated alkyl group having usually 1 to 7 carbon atoms. Specific examples of the substituents R may include methyl, ethyl, n-propyl, isopropyl, n-butyl, isobutyl, n-pentyl, n-hexyl, n-heptyl, isohexyl or the like. Among these alkyl groups, methyl, ethyl, n-propyl and isopropyl are preferred. The substituents R are not particularly restricted as long as the substituents are inactive under the reaction conditions. Typical examples of the other substituents R than the above may include alkoxy groups having 1 to 4 carbon atoms, specifically, methoxy, ethoxy, propoxy and butoxy.

The aliphatic aldehyde used in the present invention are aldehydes having two hydrogen atoms bonded to α-carbon atom thereof. Specific examples of the aliphatic aldehydes may include propionaldehyde, n-butyl aldehyde, isobutyl aldehyde, n-pentyl aldehyde, isopentyl aldehyde, n-hexyl aldehyde, isohexyl aldehyde, n-heptyl aldehyde, isoheptyl aldehyde, n-octyl aldehyde, isooctyl aldehyde, n-nonyl aldehyde, isononyl aldehyde or the like. In the case where the process includes the below-mentioned alkanal production step (A2) (the converting step of 2-substituted acrolein into alkanal), there may be suitably used aliphatic aldehydes which can readily by-produce 2-substituted acrolein, namely aliphatic aldehydes in which the carbon number of R in the above general formula is not less than 2 (i.e., aliphatic aldehydes having a larger number of carbon atoms than that of propionaldehyde).

It is preferred that the formaldehyde may be diluted with water and used in the form of an aqueous solution from the standpoint of handling property thereof. The concentration of formaldehyde is usually 5 to 60% by weight, preferably 30 to 55% by weight.

As the water-soluble bases (condensation catalysts), there may be used various bases described, for example, in Japanese Patent Application Laid-open (KOKAI) Nos. 52-124213(1977) and 4-55181(1992), German Patents Nos. 947,419 and 2,507,461, U.S. Pat. No. 3,312,736 and British Patent No. 1,317,106. Examples of these water-soluble bases may include hydroxides or carbonates of alkali metals, hydroxides or carbonates of alkali earth metals, tertiary amines or the like. These bases may be used in the form of a mixture of any two or more thereof.

As the hydroxides or carbonates of alkali metals, there may be exemplified sodium hydroxide, sodium carbonate, sodium bicarbonate, potassium hydroxide, potassium carbonate, potassium bicarbonate or the like. As the tertiary amines, there may be exemplified aliphatic, alicyclic or heterocyclic amines having usually 3 to 20 carbon atoms, preferably 3 to 15 carbon atoms. Among these amines, the aliphatic tertiary amines are preferred.

Specific examples of the aliphatic tertiary amines may include symmetrical trialkyl amines such as trimethyl amine, triethyl amine, tri-n-propyl amine, triisopropyl amine, tri-n-butyl amine, triisobutyl amine or tri-tert-butyl amine; unsymmetrical trialkyl amines such as methyldiethyl amine, dimethylethyl amine, ethyldiisopropyl amine or dimethyl-tert-butyl amine; diamines such as N,N-tetramethyl ethylene diamine or triethylene diamine; substituted amines such as N,N-dimethylcyclohexyl amine, bis(2-hydroxyethyl)cyclohexyl amine, N-methyl pyrrolidine, N-methyl piperidine, N-methyl morpholine, N,N-dimethylamino ethanol or N,N-dimethylamino neopentanol; aromatic ring-containing amines such as tribenzyl amine or N,N-dimethylbenzyl amine; tertiary amino group-containing polyamines such as triethylene diamine or bis(2-dimethylaminoethyl)methyl amine; tetra-alkyl ammoniums such as tetraethyl ammonium hydroxide; or the like. Among them, trialkyl amines are preferred.

The dimethylol alkanals produced in the alkanal production step (A1) may include, for example, dimethylol propanal in the case where propionaldehyde is used as the raw aliphatic aldehyde, or dimethylol butanal in the case where n-butyl aldehyde is used as the raw aliphatic aldehyde. Specific examples of the 2-substituted acroleins (for example, 2-alkyl acroleins) by-produced simultaneously may include 2-methyl acrolein, 2-ethyl acrolein, 2-propyl acrolein, 2-butyl acrolein, 2-pentyl acrolein, 2-hexyl acrolein or the like. The reaction conditions of the alkanal production step (A1) are described in detail hereinafter.

Next, the acrolein separation step (E) is explained. In the step (E), a 2-substituted acrolein-rich component is recovered from the reaction solution of the alkanal production step (A1). In FIG. 1, the reaction solution (4) of the alkanal production step (A1) is supplied to the acrolein separation step (E) where the reaction solution is separated into a 2-substituted acrolein-rich component (5) and a dimethylol alkanal-rich component (base-containing component) (6). The concentration of 2-substituted acrolein in the component (5) is usually 30 to 100% by weight, preferably 50 to 100% by weight. On the other hand, the concentration of dimethylol alkanal in the component (6) is usually 10 to 80% by weight, preferably 20 to 60% by weight. Specifically, as the separation methods, there may be exemplified a distillation method, a solvent extraction method or the combination of these methods which may be conducted in an appropriate order. Among them, the distillation method is preferred because of simplicity thereof. The component (5) may contain in addition to the 2-substituted acrolein, unreacted aliphatic aldehyde, formaldehyde, water, methanol and the base (condensation catalyst).

Next, the alkanal production step (A2) is explained. In the step (A2), formaldehyde is reacted with the 2-substituted acrolein recovered in the acrolein separation step (E) in a water solvent in the presence of a water-soluble base. In FIG. 1, formaldehyde (2), the 2-substituted acrolein-rich component (5) and the base (condensation catalyst) (3) are supplied to the alkanal production step (A2), whereby 2-substituted acrolein is converted into dimethylol alkanal. At least a part of a formaldehyde-containing reaction solution (18) of the alkanal production step (A2) is circulated to the alkanal production step (A1) (In FIG. 1, a whole amount of the reaction solution (18) is circulated to the step (A1)). As the water-soluble base, there may be used the same bases as used in the alkanal production step (A1). Incidentally, kinds of bases used in the alkanal production steps (A1) and (A2) may be different from each other. The reaction conditions of the alkanal production step (A2) are described in detail hereinafter.

Meanwhile, under such a condition that the molar ratio of formaldehyde to aliphatic aldehyde is 2:1 to 10:1 in the presence of the base, a considerable amount of the 2-substituted acrolein by-product is produced in addition to dimethylol alkanal. The amount of the 2-substituted acrolein by-product varies depending upon kind of the aldehyde used, kind and amount of the base used, the reaction temperature or the like. For example, in the case where n-butyl aldehyde and formaldehyde are reacted with each other at about 60° C. in the presence of triethyl amine, 2-ethyl acrolein is by-produced in an amount of about 20% by weight. Incidentally, it is known that the 2-substituted acrolein is produced by the dehydration reaction of 2-hydroxymethyl alkanal as a precursor of dimethylol alkanal, and that upon the dehydration reaction, the 2-hydroxymethyl alkanal and the 2-substituted acrolein have an equilibrium relationship to each other. Accordingly, under such a condition that the molar ratio of formaldehyde to aliphatic aldehyde is small, it is inevitable to by-produce the 2-substituted acrolein.

In the case where the molar ratio of formaldehyde to aliphatic aldehyde is more than 10:1, it is possible to suppress the production of the 2-substituted acrolein by-product, and to produce dimethylol alkanal with a high yield. However, in this case, since an excessive amount of formaldehyde remains unreacted, complicated operations are required for separation or recycle of the residual formaldehyde, resulting in increase in costs therefor. Further, since an excessive amount of formaldehyde remains in dimethylol alkanal, it is required to add a large amount of expensive oxidants in the subsequent oxidation step, and there also arises a problem that side reactions tend to be induced.

On the other hand, the 2-substituted acrolein may be converted into dimethylol alkanal by reacting with formaldehyde in the presence of the base and water. As such a conversion method, there have been proposed the following methods.

In Japanese Patent Application Laid-open (KOKAI) No. 52-124213(1977), there has been described a method of reacting 2-ethyl acrolein with an aqueous formaldehyde solution in the presence of triethyl amine, thereby obtaining dimethylol butanal. However, in this method, in order to enhance the reaction efficiency, formaldehyde must be used in an extremely excess amount based on the weight of the 2-substituted acrolein. Therefore, it is required to remove an excess amount of residual formaldehyde, which is industrially disadvantageous.

In German Patent No. 2,507,461, there has been proposed a method of reacting n-butyl aldehyde with formaldehyde, for example, in the presence of N,N-dimethylamino neopentanol in a first stage reactor, separating unreacted n-butyl aldehyde and by-produced 2-ethyl acrolein from the reaction solution by a distillation method, and adding formaldehyde and amine to the obtained distillate to conduct a second stage reaction. However, in this method, since formaldehyde is used in a stoichiometric amount, the yield of dimethylol alkanal is low.

As methods of producing dimethylol alkanoic acid by the oxidation of dimethylol alkanal, there are known an oxidation method using hydrogen peroxide (e.g., U.S. Pat. No. 3,312,736), an oxidation method using hydrogen peroxide and a catalyst composed of at least one element selected from the group consisting of cerium, titanium, zirconium, tin, niobium, molybdenum and tungsten (Japanese Patent Application Laid-open (KOKAI) No. 62-263141(1987)), an oxidation method using perisobutyric acid (Journal of Synthetic Organic Chemistry Japan, 36, 1095(1978)), or the like.

However, in any of the above-mentioned known methods, the yield of dimethylol alkanal is low, and when the dimethylol alkanal produced is oxidized, a large amount of oxidant is required since the amount of residual formaldehyde is large. Therefore, it is not possible to obtain the aimed product with a high purity and a high yield.

As described above, conventionally, there are not known any method capable of producing dimethylol alkanal with a high yield, and capable of decreasing an amount of residual formaldehyde.

In consequence, from the standpoints of reducing a load required for the recovery of unreacted formaldehyde, decreasing the amount of residual formaldehyde and producing dimethylol alkanal with a high yield, in accordance with the third preferred embodiment of the present invention, it is preferred that the molar ratio (I) of formaldehyde to aliphatic aldehyde throughout the alkanal production steps (A1) and (A2) is adjusted to 1:1 to 1:5, and the molar ratio (II) of formaldehyde to 2-substituted acrolein in the alkanal production step (A2) is adjusted to 1:3 to 1:100. Further, from the standpoint of reducing the amount of formaldehyde remaining in dimethylol alkanal, it is more preferred that the molar ratio (I) is 1:1 to 1:3 and the molar ratio (II) is 1:3 to 1:50.

The molar ratio of 2-substituted acrolein by-produced to aliphatic aldehyde charged in the alkanal production step (A1) is influenced by a molar ratio between formaldehyde and aliphatic aldehyde charged. Therefore, the molar ratio between 2-substituted acrolein and aliphatic aldehyde present in the alkanal production step (A1) is adjusted to preferably 1:0.01 to 1:2, more preferably 1:0.05 to 1:1. Under the condition that the amount of 2-substituted acrolein by-produced is small, the amount of dimethylol alkanal converted from the 2-substituted acrolein also becomes small, so that the aims of the third preferred embodiment of the present invention cannot be sufficiently accomplished. Further, when the amount of 2-substituted acrolein produced is small, the amount of formaldehyde used based on aliphatic aldehyde is necessarily increased, so that there is caused such an industrial disadvantage that a load required for the removal of excessive formaldehyde becomes large.

The amount of the base used in the alkanal production step (A1) is usually 0.01 to 1.0 mol, preferably 0.02 to 0.5 mol based on 1 mol of aliphatic aldehyde. In addition, the amount of the base used in the alkanal production step (A2) is usually 0.01 to 1.0 mol, preferably 0.02 to 0.5 mol based on 1 mol of 2-substituted acrolein.

The reaction temperatures of the respective steps vary depending upon kind and amount of the base used. For example, when hydroxides of alkali metals or alkali earth metals are used, the reaction temperature is usually −10 to 100° C., preferably 10 to 80° C. When tertiary amines are used, the reaction temperature is usually −10 to 120° C., preferably 10 to 100° C. These reactions may be conducted not only under ordinary pressure but also under reduced or increased pressure.

Next, the alkanoic acid production step (B) is explained. In the step (B), the aqueous solution (a) containing dimethylol alkanal and a base is subjected to oxidation treatment, thereby obtaining alkanoic acid. In FIG. 1, the base-containing aqueous solution (6) of the dimethylol alkanal-rich component recovered in the acrolein separation step (E), and the oxidant (7) are supplied to the alkanoic acid production step (B). In the step (B), dimethylol alkanoic acid is produced by the oxidation of dimethylol alkanal.

As the oxidation method, there may be used the above-mentioned known methods, namely an oxidation method using hydrogen peroxide (e.g., U.S. Pat. No. 3,312,736), an oxidation method using hydrogen peroxide in the presence of a catalyst composed of at least one element selected from the group consisting of cerium, titanium, zirconium, tin, niobium, molybdenum and tungsten (Japanese Patent Application Laid-open (KOKAI) No. 62-263141(1987)), an oxidation method using perisobutyric acid (Journal of Synthetic Organic Chemistry Japan, 36, 1095(1978)), or the like. Among these methods, the oxidation method using hydrogen peroxide is preferred.

The hydrogen peroxide may be used in the form of an aqueous solution containing hydrogen peroxide in an amount of usually 20 to 60% by weight. The amount of hydrogen peroxide used is usually 0.2 to 2 mol, preferably 0.4 to 1.5 mol based on 1 mol of dimethylol alkanal. The concentration of dimethylol alkanal in the oxidation reaction system is usually 5 to 60% by weight, preferably 20 to 50% by weight. The oxidation reaction temperature is usually 20 to 100° C., preferably 40 to 80° C. The above oxidation reaction is continued until no unreacted dimethylol alkanal remains in the reaction system.

Next, the alkanoic acid recovery step (C) is explained. In the step (C), dimethylol alkanoic acid is separated from the aqueous solution (b) containing the dimethylol alkanoic acid and the base. More specifically, a mineral acid is added to the above aqueous solution (b) such that the amount of the mineral acid added is not more than one equivalent based on the base (condensation catalyst) in the aqueous solution (b), thereby converting the base into a salt thereof. Successively, water in the aqueous solution (b) is replaced with an organic solvent, and after the mineral acid salt precipitated is removed, alkanoic acid is crystallized from the organic solvent solution.

According to the above crystallization method including the specified pre-treatment, it is possible to readily separate dimethylol alkanoic acid and the base converted into the mineral acid salt, from the aqueous solution containing the dimethylol alkanoic acid and the base which have a high water-solubility. In FIG. 1, the aqueous solution (8), the mineral acid (9) and the organic solvent (10) are supplied to the alkanoic acid recovery step (C), and water (11) and the mineral acid salt (12) are removed from the alkanoic acid recovery step (C). Further, the reaction mixture of the alkanoic acid recovery step (C) is subjected to liquid-solid separation, thereby separating the reaction mixture into dimethylol alkanoic acid crystals (13) and the organic solvent solution as a mother liquor (filtrate) (14).

As the mineral acids, there may be exemplified hydrochloric acid, sulfuric acid, nitric acid, phosphoric acid or the like. Among them, sulfuric acid is preferred. The amount of the mineral acid used is not more than one equivalent, preferably 0.85 to 1 equivalent based on one equivalent of the base (condensation catalyst) in the aqueous solution (b). When the amount of the mineral acid added is more than one equivalent, residual formic acid and hydroxymethyl groups are esterified together, so that the yield of dimethylol alkanoic acid is decreased. On the other hand, when the amount of the mineral acid added is too small, the salt of dimethylol alkanoic acid and base tends to be disadvantageously incorporated into the dimethylol alkanoic acid crystals.

As the methods of replacing water in the aqueous solution (b) with an organic solvent, there may be exemplified a method comprising distilling off a large portion of water in the aqueous solution (b) and then adding an organic solvent to the distillation residue; a method comprising adding an organic solvent to the aqueous solution (b) to cause phase-separation of the solution, and then removing a water phase therefrom; or the like. Further, as the method comprising distilling off water from the aqueous solution (b), there may be adopted a method of heating the aqueous solution (b) under reduced pressure, thereby distilling off water therefrom; a method comprising adding an organic solvent to the aqueous solution (b) and then evaporating water together with the organic solvent; or the like. In case of distilling off water, it is preferred that the degree of reduced pressure is controlled such that the temperature of the aqueous solution (b) is maintained at usually not more than 100° C., preferably not more than 80° C. When the temperature of the aqueous solution (b) is too high, the dehydration-condensation of dimethylol alkanoic acid tends to be caused, thereby producing an anhydride thereof, and further residual formic acid is reacted with methylol groups of dimethylol alkanoic acid, so that the yield of dimethylol alkanoic acid is decreased.

Kinds of organic solvents used are not particularly restricted as long as salts formed by the mineral acid and base (condensation catalyst) is insoluble therein but dimethylol alkanoic acid is soluble therein. For example, in the case of using dimethylol alkanoic acids other than dimethylol propionic acid, examples of suitable organic solvents may include aliphatic ketones such as acetone, methyl ethyl ketone or methyl isobutyl ketone; aliphatic esters such as ethyl acetate, propyl acetate, butyl acetate or isobutyl acetate; aliphatic nitriles such as acetonitrile or propionitrile; or the like. On the other hand, in the case of using dimethylol propionic acid, examples of suitable organic solvents may include alcohols such as methanol, ethanol, propanol or isopropyl alcohol, or the like.

In the case where dialkyl ketone is used as the above organic solvent, the following advantages can be attained. Namely, there can be produced alkanoic acid crystals which have a narrow particle size distribution and a small particle size and, therefore, are excellent in solubility and handling property upon dissolving, when used as raw materials for the production of polyesters, polyurethanes, alkyd resins or the like.

Specific examples of the dialkyl ketones may include acetone, methyl ethyl ketone, diethyl ketone, methyl n-propyl ketone, methyl isopropyl ketone, methyl n-butyl ketone, methyl isobutyl ketone, di-n-propyl ketone, diisopropyl ketone, ethyl n-propyl ketone, ethyl n-butyl ketone, ethyl isobutyl ketone, methyl n-amyl ketone, methyl isoamyl ketone, diisobutyl ketone or the like. Among these dialkyl ketones, acetone is rather disadvantageous, because acetone has a too large solubility in water so that the recovery thereof becomes difficult. From such a standpoint, unsymmetrical dialkyl ketones are preferred. Further, in view of costs, methyl isobutyl ketone is more preferred.

The amount of the organic solvent used is usually 1 to 10 times, preferably 1.5 to 5 times based on the weight of dimethylol alkanoic acid. When the amount of the organic solvent used is too large, the amount of dimethylol alkanoic acid dissolved therein is increased so that the percentage of crystallization thereof is decreased. On the other hand, when the amount of the organic solvent used is too small, the purity of dimethylol alkanoic acid produced is lowered.

When the mineral acid salt is removed from the solution whose solvent is replaced with the organic solvent, it is preferred to control the amount of water in the organic solvent solution as follows. Namely, the amount of water in the organic solvent solution is adjusted to usually not more than 5% by weight, preferably not more than 1% by weight in the case of using dimethylol alkanoic acids other than dimethylol propionic acid, or usually not more than 10% by weight, preferably not more than 5% by weight in the case of using dimethylol propionic acid. In the case where the amount of water is not controlled to such a range, there arises such a tendency that the mineral acid salt is dissolved in water and disadvantageously incorporated in the crystallized dimethylol alkanoic acid.

When the mineral acid salt precipitated from the organic solvent solution is removed by filtration, too low temperature of the organic solvent solution may cause crystallization of dimethylol alkanoic acid upon the filtration, so that the recovery efficiency of dimethylol alkanoic acid becomes low. Therefore, upon the filtration, the organic solvent solution is preferably maintained at such a temperature at which dimethylol alkanoic acid can be kept dissolved therein.

After the mineral acid salt is filtered out, the obtained filtrate is cooled for crystallization, whereby dimethylol alkanoic acid can be obtained in the form of crystals. The cooling temperature is usually 30 to −10° C., preferably 10 to −5° C. Upon the crystallization of dimethylol alkanoic acid, it is preferred that the amount of water in the organic solvent solution be adjusted to not more than 20% by weight based on the weight of the alkanoic acid. When the amount of water in the organic solvent solution is too large, the percentage of crystallization of dimethylol alkanoic acid is decreased. Further, under such a condition, since the crystallization temperature of dimethylol alkanoic acid becomes lowered, it is necessary to cool the organic solvent solution up to a lower temperature, resulting in disadvantages such as energy loss. The amount of water in the organic solvent solution is preferably not more than 10% by weight. Such a control of the amount of water in the organic solvent solution can be achieved by conducting the water amount-controlling treatment as described above with respect to the removal of mineral acid salt. Incidentally, when any mineral acid salt remains in the obtained crystals, the crystals are dissolved again in an organic solvent while heating. The obtained organic solvent solution is filtered while being kept in a hot condition, and then the resultant filtrate is subjected to recrystallization, whereby it is possible to remove a large portion of residual mineral acid salt.

Next, the alkanoic acid re-recovery step (D) is explained. In the step (D), an aqueous solution of inorganic base is added to the organic solvent solution (filtrate) recovered by solid-liquid separation after the crystallization in the above-mentioned alkanoic acid recovery step (C) and containing uncrystallized alkanoic acid, thereby converting the alkanoic acid into a salt thereof. Then, water is distilled off from a water phase separated from the organic solvent solution, thereby recovering the alkanoic acid salt. Namely, dimethylol alkanoic acid of usually 5 to 8% by weight is dissolved in the filtrate obtained in the alkanoic acid recovery step (C) and such dimethylol alkanoic acid is present in the form of a mixed solution with impurities, so that it is not possible to recover the dimethylol alkanoic acid merely by distilling off the solvent.

In consequence, in accordance with the present invention, an inorganic base is added to the above-mentioned filtrate to convert dimethylol alkanoic acid into a salt thereof, and then the resultant dimethylol alkanoic acid salt is separated and recovered from the filtrate. In FIG. 1, the filtrate (14) recovered from the alkanoic acid recovery step (C) and the aqueous solution (15) containing an inorganic base are supplied to the alkanoic acid re-recovery step (D). An organic phase (16) obtained by phase separation and water (17) distilled off from a water phase separated from the organic phase, are removed from the alkanoic acid re-recovery step (D), thereby recovering the dimethylol alkanoic acid salt (19).

As the inorganic bases, there may be suitably used bases composed of alkali metals or alkali earth metals, such as hydroxides of alkali metals, carbonates of alkali metals, hydroxides of alkali earth metals, carbonates of alkali earth metals or the like.

As the hydroxides of alkali metals, there may be exemplified sodium hydroxide, potassium hydroxide, lithium hydroxide or the like. As the carbonates of alkali metals, there may be exemplified sodium carbonate, potassium carbonate, lithium carbonate or the like. In addition, as the hydroxide of alkali earth metals, there may be exemplified calcium hydroxide, barium hydroxide or the like. As the carbonates of alkali earth metals, there may be exemplified calcium carbonate, barium carbonate or the like.

The above inorganic base is added together with water to the filtrate. The inorganic base may be used in such an amount that when added together with water, the pH of the filtrate is adjusted to usually 8 to 10, preferably 8.5 to 9.5. The temperature of the filtrate, when the inorganic base is added thereto, is usually 0 to 100° C., preferably 20 to 50° C. By stirring the filtrate, the dimethylol alkanoic acid salt in the form of an aqueous solution or solid is transferred to a water layer side and recovered therefrom. In the case where the dimethylol alkanoic acid salt is recovered in the form of an aqueous solution, water is distilled off from the aqueous solution, and if required, after a solvent in which the dimethylol alkanoic acid salt is less soluble, is added to the aqueous solution, the resultant solution is cooled and subjected to crystallization, whereby it is possible to recover the dimethylol alkanoic acid salt in the form of powder.

In the case where it is required to take out a dimethylol alkanoic acid salt powder after the alkanoic acid has been recovered in the form of an aqueous solution, water is distilled off or evaporated from the aqueous solution at a temperature of 50 to 100° C. under ordinary pressure or reduced pressure. In this case, it is preferred that the amount of water in the distillation residue be adjusted to usually not more than 10% by weight, preferably not more than 2% by weight, because the dimethylol alkanoic acid salt is extremely readily soluble in water. After distilling off water, alcohols such as methanol, ethanol, propanol or isopropanol may be added to the dimethylol alkanoic acid salt to form a dispersion thereof, followed by filtering the dispersion, whereby it is possible to obtain the dimethylol alkanoic acid salt in the form of powder.

The production process according to the present invention may be conducted in a continuous manner by referring to the process shown in FIG. 1, but may also be conducted in a batch or semi-continuous manner. When the process is conducted in a limited scale, the batch or semi-continuous process is more suitable. Especially, it is preferred that steps subsequent to the alkanoic acid recovery step (C) are conducted in a batch manner.

As described above, in accordance with the present invention, there is provided an industrially useful process for producing 2,2'-bis(hydroxymethyl)alkanoic acid, which process includes an improved step for recovery of the 2,2'-bis(hydroxymethyl)alkanoic acid. Further, in the process according to the present invention, a load required for recovery of unreacted formaldehyde can be reduced, and the amount of residual formaldehyde can be decreased, thereby obtaining the 2,2'-bis(hydroxymethyl)alkanoic acid with a high yield. Accordingly, the present invention is industrially valuable.

EXAMPLES

The present invention will now be described in more detail with reference to the following examples, but the present invention is not restricted to those examples and various modifications are possible within the scope of the invention.

Example 1

Alkanal Production Step (A1)

72 g (1 mol) of n-butyl aldehyde and 98 g (1.7 mols) of an aqueous 52 wt. % formaldehyde solution were charged into a reactor, and 10.6 g (0.08 mol) of an aqueous 30 wt. % NaOH solution was dropped into the mixed solution while heating the solution to 40° C. Thereafter, the mixed solution was reacted at a liquid temperature of 60° C. for one hour. At this time, the molar ratio between n-butyl aldehyde, formaldehyde and NaOH charged was 1:1.7:0.08.

The percentage of conversion of n-butyl aldehyde was 94 mol %; the total yield of dimethylol butanal and formaldehyde adducts of dimethylol butanal was 40 mol %; and the total selectivity of dimethylol butanal and formaldehyde adducts of dimethylol butanal was 43 mol %. Here, the formaldehyde adducts of dimethylol butanal are components which can be converted into dimethylol butanoic acid as an aimed product. Further, the yield of 2-ethyl acrolein was 23 mol %, and the amount of residual formaldehyde was 20 mol % based on the mole of n-butyl aldehyde.

Acrolein Separation Step (E)

Successively, the reaction solution of the alkanal production step (A1) was distilled at 90° C. under ordinary pressure, thereby obtaining 23 g of a 2-ethyl acrolein-rich fraction (containing 79% by weight of 2-ethyl acrolein and 21% by weight of n-butyl aldehyde) from a top of the reactor, and 158 g of a dimethylol butanal-rich fraction (an aqueous 33 wt. % dimethylol butanal solution) from the bottom of the reactor.

Alkanal Production Step (A2)

The fraction (containing 17 g (0.2 mol) of 2-ethyl acrolein) from the acrolein separation step (E) was then added to 98 g (1.7 mols) of an aqueous 52 wt. % formaldehyde solution, and while heating the obtained solution to 40° C., 2.7 g (0.02 mol) of an aqueous 30 wt. % NaOH solution was dropped thereinto. Thereafter, the liquid temperature of the obtained solution was maintained at 40° C. for one hour, thereby reacting 2-ethyl acrolein and formaldehyde. At this time, the molar ratio between 2-ethyl acrolein, formaldehyde and NaOH charged was 1:8.5:0.1.

The total yield of dimethylol butanal and formaldehyde adducts of dimethylol butanal was 70 mol % based on the mole of 2-ethyl acrolein. Further, the amount of residual formaldehyde was 140 mol % based on the mole of n-butyl aldehyde.

Second Alkanal Production Step (A1)

Next, 72 g (1 mol) of n-butyl aldehyde were added to the reaction solution obtained in the alkanal production step (A2) while maintaining at a temperature of 60° C., and 8 g (0.06 mol) of an aqueous 30 wt. % NaOH solution was dropped into the obtained solution, thereby reacting n-butyl aldehyde with unreacted formaldehyde at 40° C. for one hour. This reaction step can be regarded as such a case where the reaction solution obtained in the alkanal production step (A2) was used as a formaldehyde component in the above alkanal production step (A1).

The percentage of conversion of n-butyl aldehyde in the second alkanal production step (A1) (based on the charged amount) was 78 mol %; the total yield of dimethylol butanal and formaldehyde adducts of dimethylol butanal (based on the charged amount) was 53 mol %; and the total selectivity of dimethylol butanal and formaldehyde adducts of dimethylol butanal (based on the charged amount) was 68 mol %. In addition, the yield of 2-ethyl acrolein was 20 mol % which was approximately the same as that in the first alkanal production step (A1). Further, the amount of residual formaldehyde was 19 mol % based on the mole of n-butyl aldehyde.

The molar ratio between n-butyl aldehyde, 2-ethyl acrolein, formaldehyde and NaOH charged totally in the alkanal production step (A2) and the second alkanal production step (A1) was 1:0.2:1.7:0.8. Here, the molar ratio between 2-ethyl acrolein and formaldehyde totally charged expresses a molar ratio of the totally charged amount of 2-ethyl acrolein and formaldehyde in the alkanal production step (A2), to the charged amount of n-butyl aldehyde in the second alkanal production step (A1).

When the same operations as defined above are repeated subsequently, it is considered that the above-mentioned molar ratio between n-butyl aldehyde, 2-ethyl acrolein, formaldehyde and NaOH totally charged in the alkanal production steps (A1) and (A2) can be maintained, and the reaction therebetween can proceed in a stationary state. Thus, in the process comprising at least the alkanal production step (A1) and the alkanal production step (A2), an aimed product can be produced with a high yield even when the molar ratio of formaldehyde to n-butyl aldehyde totally charged is low.

Alkanoic Acid Production Step (B)

156 g of the fraction (an aqueous 46 wt. % alkanal solution) recovered from the bottom of a distillation tower in the acrolein separation step (E), was heated to 60° C. After 51 g (0.52 mol) of an aqueous 35 wt. % hydrogen peroxide solution was dropped into the heated fraction for 2 hours, the obtained mixture was further reacted for 5 hours. After completion of the oxidation reaction, the yield of dimethylol butanoic acid was 55 mol % based on the mole of n-butyl aldehyde consumed in the second alkanal production step (A1).

Alkanoic Acid Recovery Step (C)

7.9 g (0.038 mol; 0.95 equivalent based on NaOH) of an aqueous 47 wt. % sulfuric acid solution, was added to 200 g of the above-obtained oxidation reaction solution, thereby converting sodium derived from NaOH into sodium sulfate. Thereafter, water was distilled off from the reaction solution in a water bath maintained at 60° C., under reduced pressure. After 90 g of water was distilled off from the reaction solution, 208 g of methyl isobutyl ketone (MIBK) was added to the reaction solution, so that the amount of water in the reaction solution was adjusted to 0.7% by weight. Sodium sulfate precipitated with decrease in amount of water, was removed by filtration, and then the obtained filtrate was cooled to 0° C., thereby precipitating crystals of dimethylol butanoic acid. The percentage of crystallization of dimethylol butanoic acid was 82% by weight. The yield of dimethylol butanoic acid is 45 mol % based on the mole of the converted n-butyl aldehyde excluding recovered n-butyl aldehyde. In addition, the Na concentration in the dimethylol butanoic acid crystals was 17 ppm, and the $(SO_4)^{2-}$ concentration therein was 6 ppm. The results are shown in Table 1.

Examples 2 and 3 and Comparative Example 1

The same procedure as defined in Example 1 was conducted except that the amount of sulfuric acid used in the alkanoic acid recovery step (C) (equivalent amount based on NaOH used as a condensation catalyst) was changed as shown in Table 1, thereby obtaining crystals of dimethylol butanoic acid. The results are shown in Table 1.

TABLE 1

|  | Example 1 | Example 2 | Example 3 | Comparative Example 1 |
|---|---|---|---|---|
| $H_2SO_4$/NaOH equivalent | 0.95 | 1.00 | 0.90 | 1.15 |
| Yield of dimethylol butanoic acid (mol %) (based on n-butyl aldehyde) | 45 | 40 | 43 | 26 |
| Na concentration in crystal (ppm) | 17 | 14 | 16 | 150 |
| $(SO_4)^{2-}$ concentration in crystal (ppm) | 6 | 27 | 5 | 440 |

Example 4
Alkanal Production Step (A1) and Alkanoic Acid Production Step (B)

73 g (1.2 mols) of propionaldehyde and 173 g (3 mols) of an aqueous 52 wt. % formaldehyde solution were charged into a reactor. While heating the obtained mixture to 25° C., 48 g (0.09 mol) of an aqueous 20 wt. % $Na_2CO_3$ solution was dropped thereinto for 2 hours. Thereafter, the reaction solution was heated to 70° C. for 30 minutes, and 140 g (1.44 mols) of an aqueous 35 wt. % hydrogen peroxide solution was dropped into the reaction solution for 4 hours. After completion of the dropping, the reaction solution was further stirred for 4 hours.

Alkanoic Acid Recovery Step (C)

Successively, 18.5 g (0.09 mol; 0.99 equivalent based on $Na_2CO_3$) of an aqueous 47 wt. % sulfuric acid solution was added to the above reaction solution at 40° C. Then, 244 g of water was distilled off from the reaction solution, under reduced pressure. Further, while 678 g of methanol was dropped into the thus-concentrated reaction solution, water remaining in the reaction solution was distilled off together with methanol therefrom at a temperature of 49 to 68° C. under slightly reduced pressure. 294 g of methanol was further added to the obtained distillation residue. At this time, the amount of water in the obtained solution was 1.07% by weight. Further, the precipitation of crystals was observed in the solution, and the crystals precipitated was determined to be a mixture composed of sodium sulfate crystals and dimethylol propionic acid crystals. The solution was heated to 60 to 70° C., thereby dissolving dimethylol propionic acid crystals therein.

The above solution was filtered through a glass filter to remove sodium sulfate therefrom. The resultant filtrate was distilled and concentrated under slightly reduced pressure, thereby recovering 191 g of methanol. After 13 g of water and 33 g of methanol were added to the distillation residue to control the concentration thereof, the obtained solution was cooled to 0° C. while stirring, so that dimethylol propionic acid crystals were precipitated. At this time, the yield of dimethylol propionic acid was 48 mol %. In addition, the Na concentration in the dimethylol propionic acid crystals was 78 ppm, and the $(SO_4)^{2-}$ concentration therein was 22 ppm. Further, when the above crystals were recrystallized from water, it was determined that the Na concentration in the crystals was 8.2 ppm, and the $(SO_4)^{2-}$ concentration therein was 6.2 ppm. The results are shown in Table 2.

Examples 5 and 6

The same procedure as defined in Example 4 was conducted except that the amount of sulfuric acid (equivalent amount based on $Na_2CO_3$ used as a condensation catalyst) used in the alkanoic acid recovery step (C) was changed as shown in Table 2, thereby obtaining dimethylol propionic acid crystals. The results are shown in Table 2.

Comparative Example 2

The same procedure as defined in Example 4 was conducted except that the amount of sulfuric acid based on sodium carbonate used as a condensation catalyst was changed to 1.02 equivalents. Although it was attempted to obtain dimethylol butanoic acid crystals, a large portion of the obtained product was methyl dimethylol-propionate. The results are shown in Table 2.

TABLE 2

|  | Example 4 | Example 5 | Example 6 | Comparative Example 2 |
|---|---|---|---|---|
| $H_2SO_4$/$Na_2CO_3$ equivalent | 0.99 | 0.97 | 0.95 | 1.02 |
| Yield of dimethylol propionic acid (mol %) (based on propionaldehyde) | 48 | 46 | 44 | 4 |

TABLE 2-continued

|  | Example 4 | Example 5 | Example 6 | Comparative Example 2 |
|---|---|---|---|---|
| Na concentration in crystal (ppm) | 78 | 190 | 170 | — |
| $(SO_4)^{2-}$ concentration in crystal (ppm) | 22 | 10 | 23 | — |
| Na concentration after recrystallization (ppm) | 8 | 21 | 22 | — |
| $(SO_4)^{2-}$ concentration after recrystallization (ppm) | 6 | 8 | 7 | — |

Example 7

The same procedure as defined in Example 1 was conducted except that a sodium salt of dimethylol butanoic acid was recovered from a filtrate from which dimethylol butanoic acid crystals have been separated by filtration, in the following manner, thereby producing dimethylol butanoic acid crystals. Specifically, 62 g of an aqueous 20 wt. % NaOH solution was dropped into the above filtrate containing dimethylol butanoic acid in an amount of 6% by weight (corresponding to 10 mol % based on the mole of the converted n-butyl aldehyde excluding recovered n-butyl aldehyde), and the solution was stirred. The pH of the solution was 9.0.

Successively, the above solution was allowed to stand, whereby the solution was separated into two layers from which only a water layer as a lower layer was recovered. Water was distilled off from the recovered aqueous solution, under reduced pressure. When the amount of water in the distillation residue reached 1.2% by weight, 131 g of methanol was added to the distillation residue, and the resultant solution was heated to 65° C. while stirring, thereby dispersing a sodium salt of dimethylol butanoic acid therein. Thereafter, the resultant dispersion was cooled to 5° C. and filtered to remove the sodium salt of dimethylol butanoic acid therefrom. The yield of the sodium salt of dimethylol butanoic acid was 9 mol % based on the mole of converted n-butyl aldehyde excluding recovered n-butyl aldehyde, and the percentage of recovery of the sodium salt of dimethylol butanoic acid from the filtrate was 93% by weight.

Meanwhile, in order to determine what effects were obtained due to difference in kinds of organic solvents used upon crystallization, the following experiments were conducted.

First, dimethylol butanoic acid crystals recovered in Example 1 were spread over a batt and dried at 60° C. for 24 hours under reduced pressure. The obtained dry crystals were passed through a sieve to measure a particle size distribution thereof, and were tested to determine solubility thereof in various solvents. Further, the same procedure as defined in Example 1 was conducted except that the organic solvent used upon crystallization was changed from MIBK to ethyl acetate, thereby producing dimethylol butanoic acid crystals. The thus-obtained crystals were subjected to the same experiments as above. The results of measurements concerning a particle size distribution are shown in Table 3, and the results of solubility tests are shown in Table 4.

TABLE 3

|  | Crystallization solvent | Particle size and wt. % | | | | |
|---|---|---|---|---|---|---|
|  |  | Less than 1 mm | 1 to 4 mm | 4 to 10 mm | 10 to 30 mm | More than 30 mm |
| Example 1 | MIBK | 83.1 | 4.0 | 8.3 | 2.7 | 1.9 |
| Reference Example 1 | Ethyl acetate | 28.4 | 21.1 | 25.4 | 18.2 | 6.9 |

TABLE 4

|  | Crystallization solvent | Dissolving time (min.) | | | |
|---|---|---|---|---|---|
|  |  | Acetone | Methyl ethyl ketone | N-methyl pyrrolidone | Ethyl acetate |
| Example 1 | MIBK | 20 | 25 | 50 | 300 |
| Comparative Example 1 | Ethyl acetate | 56 | 240 | 91 | 1,080 |

As is apparent from Table 3, by using dialkyl ketone as a crystallization solvent, the obtained alkanoic acid crystals showed a sharper particle size distribution (less secondary coagulation) and a small particle size. As shown in Table 4, such alkanoic acid can be rapidly dissolved in various organic solvents.

What is claimed is:

1. A process for producing 2,2'-bis(hydroxymethyl) alkanoic acid, comprising:

a 2,2'-bis(hydroxymethyl)alkanal production step (A1) of reacting aliphatic aldehyde having two hydrogen atoms bonded to α-carbon atom thereof, with formaldehyde in the presence of a water-soluble base;

a 2,2'-bis(hydroxymethyl)alkanoic acid production step (B) of subjecting the thus obtained aqueous solution (a) containing 2,2'-bis(hydroxymethyl)alkanal and the base to oxidation treatment; and an alkanoic acid recovery step (C) of separating 2,2'-bis (hydroxymethyl)alkanoic acid from the thus obtained aqueous solution (b) containing the 2,2'-bis (hydroxymethyl)alkanoic acid and the base, in the alkanoic acid recovery step (C), a mineral acid being added to the aqueous solution (b) in an amount of not more than one equivalent based on the base in the aqueous solution (b) to convert the base into a salt thereof, water in the aqueous solution (b) being replaced with an organic solvent to form an organic solvent solution, and after removing the mineral acid salt precipitated from the organic solvent solution, 2,2'-bis(hydroxymethyl) alkanoic acid being crystallized from the organic solvent solution.

2. A process according to claim 1, wherein the amount of the mineral acid added to the aqueous solution (b) is 0.85 to 1.00 equivalent based on the base in the aqueous solution (b).

3. A process according to claim 1, wherein the amount of water in the organic solvent solution upon crystallization of the alkanoic acid, is adjusted to not more than 20% by weight based on the weight of the alkanoic acid.

4. A process according to claim 1, further comprising an alkanoic acid re-recovery step (D) of adding an aqueous solution containing an inorganic base to the organic solvent solution recovered by solid-liquid separation after crystallization of the alkanoic acid and containing uncrystallized alkanoic acid to convert the uncrystallized alkanoic acid into a salt thereof, and then distilling off water from a water phase separated from the organic solvent solution, thereby recovering the salt of alkanoic acid.

5. A process according to claim 1, further comprising a 2,2'-bis(hydroxymethyl)alkanal production step (A2) of reacting formaldehyde with 2-substituted acrolein by-produced in the alkanal production step (A1) in a water solvent in the presence of a water-soluble base.

6. A process according to claim 1, wherein said organic solvent used upon the crystallization, is dialkyl ketone.

7. A process according to claim 6, wherein said dialkyl ketone is methyl isobutyl ketone.

8. A process according to claim 1, further comprising an acrolein separation step (E) of recovering a 2-substituted acrolein-rich component from the reaction solution of the alkanal production step (A1), and a 2,2'-bis(hydroxymethyl) alkanal production step (A2) of reacting formaldehyde with 2-substituted acrolein recovered in the alkanal production step (A1) in a water solvent in the presence of a water-soluble base, at least a part of the formaldehyde-containing reaction solution of the alkanal production step (A2) being circulated to the alkanal production step (A1), the molar ratio (I) of formaldehyde to aliphatic aldehyde having two hydrogen atoms bonded to α-carbon atom thereof throughout the alkanal production steps (A1) and (A2) being adjusted to 1:1 to 1:5, and the molar ratio (II) of formaldehyde to the 2-substituted acrolein in the alkanal production step (A2) being adjusted to 1:3 to 1:100.

* * * * *